United States Patent

Kobayashi et al.

[11] Patent Number: 6,037,155
[45] Date of Patent: Mar. 14, 2000

[54] PROCESS FOR PREPARING α-HYDROXY ACIDS USING MICROORGANISM AND NOVEL MICROORGANISM

[75] Inventors: Yoichi Kobayashi, Fujiwasa; Ken Watabe; Mahito Ohira, both of Yokohama; Koichi Hayakawa, Hiratsuka, all of Japan

[73] Assignee: Nippon Soda Co., Ltd., Tokyo, Japan

[21] Appl. No.: 09/125,150

[22] PCT Filed: Feb. 27, 1997

[86] PCT No.: PCT/JP97/00578

§ 371 Date: Aug. 11, 1998

§ 102(e) Date: Aug. 11, 1998

[87] PCT Pub. No.: WO97/32030

PCT Pub. Date: Sep. 4, 1997

[51] Int. Cl.[7] .................. C12P 7/42; C12N 1/20
[52] U.S. Cl. .............. 435/128; 435/146; 435/252.1; 435/822; 435/830
[58] Field of Search ............... 435/128, 146, 435/822, 830; 438/252.1

[56] References Cited

U.S. PATENT DOCUMENTS

| | | | |
|---|---|---|---|
| 5,296,373 | 3/1994 | Endo et al. | 435/129 |
| 5,508,181 | 4/1996 | Hashimoto et al. | 435/129 |
| 5,736,385 | 4/1998 | Tamura et al. | 435/146 |

FOREIGN PATENT DOCUMENTS

| | | | |
|---|---|---|---|
| 0 610 049 A2 | 8/1994 | European Pat. Off. | |
| 61056086 | 8/1984 | Japan | |
| 4-40898 | of 1987 | Japan | C12P 7/42 |
| 63-222696 | of 1987 | Japan | C12P 7/42 |
| 4-99497 | of 1990 | Japan | C12P 1/00 |
| 5-192189 | of 1991 | Japan | C12P 11/00 |
| 7-213296 | of 1994 | Japan | C12P 7/42 |
| 81713175 | 12/1994 | Japan | |
| 9028390 | 7/1995 | Japan | |
| 4040897 | 6/1998 | Japan | |
| WO 96/09403 | 3/1996 | WIPO | |

*Primary Examiner*—Herbert J. Lilling
*Attorney, Agent, or Firm*—Dennis G. LaPointe; Joseph C. Mason, Jr.; Mason & Associates, PA

[57] ABSTRACT

A process for preparing α-hydroxy acids represented by the general formula (II): RCH(OH)COOH (wherein R represents a hydrogen atom, an optionally substituted C1–C6 alkyl group, an optionally substituted C2–C6 alkenyl group, an optionally substituted C1–C6 alkoxy group, an optionally substituted aryl group, an optionally substituted aryloxy group, or an optionally substituted heterocyclic group) by allowing a microorganism to act on α-hydroxy nitriles (I): RCH(OH)CN (wherein R is as defined above) to hydrolyze and convert the α-hydroxy nitrites to α-hydroxy acids (II), wherein the α-hydroxy acids (II) are produced and accumulated in an aqueous solvent by a microorganism having the concentration resistance to the α-hydroxy nitrites (I) and/or α-hydroxy acids (II) and durability preferably in the presence of a cyanide, and harvested. According to this process, the use of the microorganism having the concentration resistance to the α-hydroxy nitriles (I) and/or α-hydroxy acids (II) and durability high enough to permit the activity to persist for a long period of time enables α-hydroxy acids (II) to be accumulated in high concentrations and cell bodies to be repeatedly used, and hence enables α-hydroxy acids (II) to be efficiently prepared. The addition of a cyanide to the reaction system results in more efficient preparation of α-hydroxy acids (II).

9 Claims, No Drawings

PROCESS FOR PREPARING α-HYDROXY ACIDS USING MICROORGANISM AND NOVEL MICROORGANISM

FIELD OF INVENTION

The present invention relates to a process to prepare α-hydroxy acid based on hydrolysis of hydroxy nitrile by means of using microorganisms and novel microorganisms. Among α-hydroxy acids, lactic acid is useful for foods, brewing and other industrial uses, while 2-hydroxy-4-methylthiobutyric acid is useful as a feed additive for livestock.

BACKGROUND OF ART

In the past, the following methods have been known as a method for preparing α-hydroxy acid [II] by using α-hydroxynitrile [I] as the starting material and by means of using microorganisms.

(1) A method for preparing lactic acid, glycolic acid, etc. by using a microorganism, such as Bacillus spp., Bacterizium spp., Micrococcus spp. and Brevibacterium spp., which is disclosed in Japanese Patent Publication No. Sho 58-15120.

(2) A method for preparing lactic acid, glycolic acid and 2-hydroxyisobutyric acid by using a microorganism belonging to Corynebacterium spp., which is disclosed in Japanese Patent Laid-open No. Sho 61-56086.

(3) A method for preparing lactic acid, 2-hydroxyisobutyric acid, 2-hydroxy-2-hydroxyphenyl propionic acid and mandelic acid by using a microorganism, such as Pseudomonas spp., Arthrobacter spp., Aspergillus spp., Penicillium spp., Cocryoboros spp. and Fusarium spp., which is disclosed in Japanese Patent Laid-open No. Sho 63-222696.

(4) A method for preparing 2-hydroxy-3,3-dimethyl-4-butyrolactone by using a microorganism, such as Arthrobacter spp., Aspergillus spp., Bacillus spp., Bacterizium spp., Brevibacterium spp., Cocryoboros spp., Corynebacterium spp., Micrococcus spp., Nocardia spp., Penicillium spp., Pseudomonas spp. and Fusarium spp., which is disclosed in Japanese Patent Laid-open No. Sho 64-10996.

(5) A method for preparing 2-hydroxyisobutyric acid by using a microorganism, such as Rhodococcus spp., Pseudomonas spp., Arthrobacter spp. and Brevibacterium spp., which is disclosed in Japanese Patent Laid-open No. Hei 4-40897.

(6) A method for preparing α-hydroxy-4-methylthiobutyric acid by using a microorganism, such as Caseobater spp., Pseudomonas spp., Alcaligenes spp., Corynebacterium spp., Brevibacterium spp., Nocardia spp., Rhodococcus spp. and Arthrobacter spp., which is disclosed in Japanese Patent Laid-open No. Hei 4-40898.

(7) A method for preparing 4-methylthiobutyric acid by using a microorganism, such as Alcaligenes spp., Rhodococcus spp. and Goldona spp., which is disclosed in WO 96/09403.

(8) A method for preparing α-hydroxy-4-methylthiobutyric acid by using a microorganism, such as Pantoea spp., Micrococcus spp. and Bacterizium spp., which is disclosed in Japanese Patent Laid-open No. Hei 8-173175.

However, the methods for preparing α-hydroxy acid as mentioned above are not always recognized as satisfactory one which can produce and accumulate an objective substance at a high concentration. For example, in case of lactic acid, only 9.8% by weight accumulation thereof is recognized when one of Corynebacterium spp. is used as the microorganism (Japanese Patent Laid-open No. Sho 61-56086), only 10% by weight accumulation thereof is recognized when one of Pseudomonas spp. is used (Japanese Patent Laid-open No. Sho 63-222696) and only 0.15% by weight accumulation thereof is recognized when one of Arthrobacter spp. is used (Japanese Patent Laid-open No. Sho 63-222696). Whereas, the accumulation of α-hydroxyisobutyric acid by using one of Pseudomonas spp. is found to be as much as 0.8% by weight (Japanese Patent Laid-open No. Sho 63-222696), the accumulated amount of α-hydroxy-4-methylthiobutyric acid is found to be 188 mM (2.8% by weight) by using one of Caseobater spp. (Japanese Patent Laid-open No. Hei 4-40898), 55 mM (0.8% by weight) by using one of Arthrobacter spp. (Japanese Patent Laid-open No. Hei 4-40898) and 940 mM (14% by weight) by using one of Alcaligenes spp. (WO 96/09403), respectively.

As a reason for the low accumulation concentration of such products as described above, it is considered that some enzymatic activity relating thereto might be inhibited in the presence of cyanic acid (Agricultural Biological Chemistry, Vol.46, page 1165, 1982) which is generated in the partial dissociation of α-hydroxy nitrile in water together with the corresponding aldehyde or ketone (Chemical Reviews, Vol.42, Page 189, 1948). Further, a possibility that the related-enzyme is inactivated in a short time with the dissociated-aldehyde has been also pointed out. As a solution to prevent such inactivation of the enzyme, a method to add either acidic sulfite ions or dithionite ions (Japanese Patent Laid-open No. Hei 5-192189) and a method to add either phosphite ions or hypophosphite ions (Japanese Patent Laid-open No. Hei 7-213296) have been proposed. However, the concentration of α-hydroxy acid produced and accumulated is not so high even by using such additives as described above.

In general, when accumulated-concentration of a product remains low, it is well known to the specialists in the art that the installation for such manufacturing tend to be complex and large. Therefore, there has been difficulty in the efficiency to manufacture α-hydroxy acid in an industrial scale according to the methods as described above. The present invention is to provide a method to accumulate α-hydroxy acid at a high concentration level by means of using microorganisms and to efficiently produce α-hydroxy acid.

DISCLOSURE OF THE INVENTION

The inventors of the present invention had made screening studies in order to find industrially-advantageous microorganisms which enzymatically convert α-hydroxy nitrites represented by a general formula [I]; RCH(OH)CN (wherein R represents a hydrogen atom, an optionally-substituted C1–C6 alkyl group, an optionally-substituted C2–C6 alkenyl group, an optionally-substituted C1–C6 alkoxy group, an optionally-substituted aryl group, an optionally-substituted aryloxy group, or an optionally-substituted heterocyclic group) to α-hydroxy acids represented by a general formula [II]; RCH(OH)COOH (wherein R is as defined above), of which converting activity is resistant to the suppressing effect of α-hydroxy nitrile [I] or α-hydroxy acid [II], and have durability to maintain such converting activity for a long time and capability to accumulate an α-hydroxy acid [II] to a high concentration level.

As a result, the inventors ultimately found such desired activity as described above in microorganisms which belong to Variovorax spp. and Arthrobacter spp. Furthermore, they have found that the enzymatic activity described above can be improved by adding a cyanide substance represented by a general formula [III]; Mm(CN)n (wherein M represents a hydrogen atom, ammonium or a metal ion, and m and n represent an integer 1, 2 or 3) into the reaction system to achieve the present invention.

Consequently, the present invention relates to a process for preparing α-hydroxy acid [II] characterized in that α-hydroxy acid [II] is produced, accumulated and harvested in an aqueous solvent in the presence of microorganisms having both concentration resistance and durable property to α-hydroxy nitrile [I] and/or α-hydroxy acid [II] in the process for preparing α-hydroxy acid [II] wherein the α-hydroxy nitrile [I] is hydrolyzed by the microbial reactions to thereby be converted to α-hydroxy acid [II], and a cyanide compound is added to the said reaction system.

The present invention is now further described in detail.

As the microorganisms to be used in the present invention, any one can be applied without particular limitation if the one can maintain its concentration resistance to either α-hydroxy nitriles or α-hydroxy acids to the extent required for achieving the object of the present invention and has durability to maintain the enzymatic activity for a long period. As the examples for such microorganisms, *Variovorax paradoxus* IAM 12374 strain and Arthrobacter NSSC 104 strain (FERM P-15424) are given. *Variovorax paradoxus* IAM 12374 strain is easily obtainable from Institute for Molecular Cell Biology, Tokyo University (IAM). Whereas, Arthrobacter NSSC 104 strain has been newly isolated from the nature world by the inventors of the present invention and has been deposited with the following details.

Deposition No.: FERM BP-5829 (Transferred from Bikouken Microorganism Deposition No. P-15424)

Date of Deposition: Domestic deposition has been made on Feb. 6, 1996 and international deposition has been made on Feb. 20, 1997.

Place of Deposition: No. 1-3, Higashi 1-chome, Tsukuba-shi, Ibaragi, Japan

Organization for Deposition: Institute for Biotechnology and Industrial Technology, Industrial Technology Academy, Ministry of trade and Industries Whereas, the microbiological property of Arthrobacter NSSC 104 strain is as follows.

Shape: Polymorphous bacillus
Gram's stain property: Positive
Rod-coccus cycle: Positive
Spores formation: Negative
Mobility: Negative
Diamino acid in Cell Wall: Lysine
Oxigen requirement: Aerobic
Oxidase formation: Negative
Catalase formation: Positive
DNA decomposition: Positive
Liquefaction of Gelatin: Positive
Starch decomposition: Positive
Casein decomposition: Positive
Vitamins requirement: Negative
Glycolyl test: Negative (Acetyl-type)
Quinone type: MK-9 (H2)
Sugar composition of Cell Wall: Galactose + Glucose +

After referring the microbiological properties of the NSSC 104 strain according to Bergey's Manual of Systematic Bacteriology (1986), the strain was identified as a bacterial strain belonging to Arthrobacter spp. The strain has been deposited with the deposition No. mentioned above in Institute for Biotechnology and Industrial Technology, Industrial Technology Academy, Ministry of Trade and Industries.

Now, the embodiments for carrying out the present invention are described herein below.

Cultivation of the microorganisms used in the present invention is carried out on an ordinary medium wherein enzyme-induction substance, carbon source being utilizable by the microorganisms, nitrogen source, inorganic ions and organic nutrients, if required, are contained. As the examples for the enzyme induction substance usable in the present invention, nitrile compounds including isobutyronitrile and the like and cyclic amide compounds including ε-caprolactam and the like are given. As the carbon source, carbohydrates including glucose and the like, alcohols including ethanol and the like, organic acids and so on are used if required. As the nitrogen source, amino acids, nitrates, ammonium salts and the like are used. As the inorganic ions, phosphate ions, potassium ions, magnesium ions, sulfate ions, ferric ions and the like are used depending upon the requirement. As the organic nutrients, vitamines, amino acids, etc. and corn steep liquer containing the same, yeast extracts, polypeptone, bouillon extracts and the like are used, if required. The cultivation is carried out by properly maintaining the medium condition, pH to a range from 6 to 9, temperature to a range of from 25 to 37° C. and under an aerobic condition.

The hydrolysis reaction caused by microorganisms according to the present invention is proceeded by collecting the cultivated microorganism cells as described above, preparing processed-microorganism cells, such as immobilized cells, crude enzymes and immobilized enzymes, and contacting the processed-microorganisms to α-hydroxy nitrile [I] in an aqueous solvent. When immobilizing microorganism cells or enzymes, a normal immobilization method, such as carrier binding method and entrapping method, can be applied. When preparing crude enzymes, enzyme purification methods customarily employed, such as ammonium sulfate salting out and chromatography, can be applied after crushing microorganism cells by using ultrasonic waves, high-pressure homogenizer or the like. The microorganism cells is used for the hydrolysis reaction at a dose of 0.01–10% by weight on dry weight basis, and the cells can be repeatedly used by recovering them by any means of filtration, centrifugation and ultrafiltration membrane concentration method after the completion of the reaction. As the aqueous solvent, either water or aqueous solution containing minerals such as buffer and an organic solvent can be used, and said aqueous solution may be separated into two layers.

R contained in α-hydroxy nitrile represented by the general formula [I]; RCH(OH)CN, in the present invention represents a hydrogen atom, an optionally-substituted C1–C6 alkyl group, an optionally-substituted C2–C6 alkenyl group, an optionally-substituted C1–C6 alkoxyl group, an optionally-substituted aryl group, an optionally-substituted aryloxy group or an optionally-substituted heterocyclic group.

More specifically, R can be a hydrogen atom, a C1–C6 alkyl, such as methyl, ethyl, propyl, isopropyl, butyl, sec-butyl, t-butyl, pentyl and hexyl, a C1–C6 alkylthio C1–C6 alkyl, such as methylthiomethyl, 1-methylthioethyl, 2-methylthioethyl, 1-methylthiopropyl, 2-methylthiopropyl, 3-methylthiopropyl, 1-methylthiobutyl, 2-methylthiobutyl, 3-methylthiobutyl, 4-methylthiobutyl, 6-methylthiohexyl, ethylthiomethyl, 1-ethylthioethyl, 2-ethylthioethyl, 1-ethylthiopropyl, 2-ethylthiopropyl, 3-ethylthiopropyl, 1-ethylthiobutyl, 2-ethylthiobutyl, 3-ethylthiobutyl, 4-ethylthiobutyl, propylthiomethyl, 1-propylthioethyl, 2-propylthioethyl, 1-propylthiopropyl, 2-propylthiopropyl, 3-propylthiopropyl, 1-methylthioisopropyl, 1-ethylisopropyl, 1-propylthiobutyl, 2-propylthiobutyl, 3-propylthiobutyl, 4-propylthiobutyl, propylthiomethyl, 1-propylthioethyl, 2-propylthioethyl, 1-isopropylthiopropyl, 2-isopropylthiopropyl, 3-isopropylthiopropyl, 1-isopropylthiobutyl, 2-isopropylthiobutyl, 3-isopropylthiobutyl and 4-isopropylthiobutyl, a hydroxy C1–C6 alkyl, such as hydroxymethyl, 1-hydroxyethyl, 2-hydroxyethyl, 1-hydroxypropyl, 2-hydroxypropyl, 3-hydroxypropyl, 1-hydroxybutyl, 1-hydroxyisopropyl, 2-hydroxybutyl and 3-hydroxybutyl, a carboxy C1–C6 alkyl, such as carboxymethyl, 2-carboxyethyl, 1-carboxyethyl, 3-carboxypropyl, 2-carboxypropyl and 1-carboxypropyl, a carbamoyl C1–C6 alkyl, such as carbamoylmethyl, 1-carbamoylethyl, 2-carbamoylethyl, 1-carbamoylpropyl, 2-carbamoylpropyl and 3-carbamoylpropyl, a mercapto C1–C6 alkyl, such as mercaptomethyl, 1-mercaptoethyl, 2-mercaptoethyl, 1-mercaptopropyl, 2-mercaptopropyl and 3-mercaptopropyl, a carbamidino C1–C6 alkyl, such as carbamidinomethyl, 1-carbamidinoethyl, 2-carbamidinoethyl, 1-carbamidinopropyl, 2-carbamidinopropyl and 3-carbamidinopropyl, an optionally-substituted C1–C6 aralkyl, such as benzyl, 2-chlorobenzyl, 4-methylbenzyl, 4-methoxybenzyl, 3-nitrobenzyl, 4-hydroxybenzyl, α-methylbenzyl and α,α-dimethylbenzyl, a C1–C6 alkyl substituted with a heterocyclic ring, such as 3-indolylmethyl, 2-indolylmethyl, 2-(3-indolyl)ethyl, 1-(3-indolyl)ethyl, 2-indolylmethyl, 2-(2-indolyl)ethyl, 1-(2-indolyl)ethyl, 4-imidazolylmethyl, 2-imidazolylmethyl, 1-(4-imidazolyl)ethyl and 2-(4-imidazolyl)ethyl, an optionally-substituted C2–C6 alkenyl, such as vinyl, propenyl, isopropenyl, allyl, 1-chloroallyl, 2-chloroallyl and crothyl, an optionally-substituted C1–C6 alkoxyl, such as methoxy, ethoxy, propoxy and trifluoromethoxy, an optionally-substituted aryl, such as phenyl, 2-chlorophenyl, p-tolyl, 3-nitrophenyl, 4-cyanophenyl, α-naphthyl and β-naphthyl, an optionally-substituted aryloxy, such as phenyloxy, 2-chlorophenyloxy, p-tolyloxy, 3-nitrophenyloxy, α-naphthyloxy and β-naphthyloxy, or, a 3–7 membered heterocyclic group which contains at least one atom selected from a group consisting of nitrogen atom, oxygen atom and sulfur atom as hetero atom, such as 2-pyridyl, 3-pyridyl, 4-pyridyl, 5-chloro-3-pyridyl, 2-thienyl, 3-thienyl, 2-pyrrolyl, 3-pyrrolyl, 2-furyl and 3-furyl.

As more specific examples for the α-hydroxy nitrile [I], lactonitrile, mandelonitrile, 2-hydroxy-4-methylthiobutyronitrile and the like can be given.

The α-hydroxy nitrile [I] is used in the reaction at a concentration of 0.1–50% by weight and may be added further during the process of the reaction when required. pH of the reaction solution shall be kept in a range of from 5 to 11 by using either appropriate buffers or acid and alkali. The reaction is preferably proceeded at a temperature of from 4 to 50° C., more preferably from 20 to 40° C.

As the examples for the cyanide compounds used in the present invention and represented by a general formula [III], hydrogen cyanide, sodium cyanide, potassium cyanide, calcium cyanide, magnesium cyanide, tarium cyanide, ammonium cyanide and the like are given. The cyanide compound is normally used in the reaction at a concentration of from 0.4 to 1000 mM, preferably from 4 to 500 mM and may be added further during the reaction when required.

Consequently, α-hydroxy acid [II] corresponding to α-hydroxy nitrile [I] which is added for a period of from 6 to 120 hours is accumulated as the ammonium salt thereof at a concentration of 15% by weight or more. The microorganism cells used in the reaction can be repeatedly used for the hydrolysis reaction without substantial loss of enzymatic activity.

The product obtained can be isolated and purified according to a customarily-employed method, such as concentration and extraction, and the product can be separated from ammonium by means of extraction with an organic solvent, thermal decomposition or the like, if required. As the examples for the product, that is α-hydroxy acid represented by the formula [II], lactic acid, mandelic acid, 2-hydroxy-4-methylthiobutyric acid and the like are given.

BEST MODE FOR CARRYING OUT THE INVENTION

The present invention is further explained in detail with referring the following examples.

EXAMPLE 1

A medium in an amount of 2 ml containing 0.3% buillon, 0.5% pepton and 0.5% sodium chloride was placed in a test tube, and the other medium in an amount of 20 ml having a composition as mentioned below was placed in a 100 ml triangular-shaped flask with buffles, then both media were sterilized for 15 minutes at 121° C., respectively. One loop amount of IAM 12374 strain of *Variovorax paradoxus* was inoculated into the test tube containing 2 ml medium and the strain was cultivated under continuous shaking condition for over night at 30° C., then 0.2 ml of the medium was transferred to the triangular-shaped flask with buffles. The transferred-medium was further cultivated at 30° C. for 3 days. The cultivated-medium was then subjected to centrifugation process, and the microorganism cells obtained was washed with saline. The microorganism cells was then suspended into 0.1 M phosphate buffer solution (pH 7.5) to prepare 0.1% by weight solution on dry weight basis. Then, 2-hydroxy-4-methylthiobutyronitrile was added into the phosphate buffer solution to prepare 160 mM solution thereof as final concentration and hydrolysis reaction of the solution was proceeded at 30° C. with mild shaking. After the addition, the same amount of 2-hydroxy-4-methylthiobutyronitrile was further added 9 times to the buffer solution at an interval of 12 hours to carry out the reaction for total duration of 120 hours. After the completion of the reaction, the reacted-solution was subjected to a centrifugation process to remove the microorganism cells and the concentration of 2-hydroxy-4-methylthiobutyric acid contained in the supernatant was determined by using high performance liquid chromatography (Column: TSK gel ODS-80TM, Carrier: acetonitrile/water/trifluoroacetic acid=20/80/0.1). The accumulation of 2-hydroxy-4-methylthiobutylate ammonium at a level of 25% by weight was thereby confirmed. The yield was found to be 98%.

Yeast Extract 0.5%
Glycerol 0.5%
Monopotassium phosphate 0.1%
Dipotassium phosphate 0.1%
NaCl 0.02%
Magnesium sulfate 7 hydrate 0.02%
ε-caprolactam 0.5%
pH 7.2 (Adjusted with 2N sodium hydroxide)

EXAMPLE 2

A medium in an amount of 2 ml containing 0.3% buillon, 0.5% pepton and 0.5% sodium chloride was placed in a test tube, and the other medium in an amount of 20 ml having a composition as mentioned below was placed in a 100 ml triangular-shaped flask with buffles, then both media were sterilized for 15 minutes at 121° C., respectively. One loop amount of NSSC 104 strain of Arthrobacter spp. was inoculated into the test tube containing 2 ml medium and the strain was cultivated under continuous shaking condition for a night at 30° C., then 0.2 ml of the medium was transferred to the triangular-shaped flask with a buffle. The transferred-medium was further cultivated under continuous shaking condition at 30° C. for 5 days. The cultivated-medium was then subjected to centrifugation process, and the microorganism cells obtained was washed with saline. The microorganism cells was then suspended into 0.1 M phosphate buffer solution (pH 7.5) to prepare 0.6% by weight solution thereof on dry weight basis. Then, lactonitrile was added into the phosphate buffer solution to thereby prepare 124 mM buffer solution as its final concentration and the buffer solution was then subjected to hydrolysis reaction at 30° C. with mild shaking. After the addition, the same amount of lactonitrile was further added 20 times to the buffer solution at an interval of 5 hours to carry out the reaction for total duration of 100 hours. After the completion of the reaction, the reacted-solution was subjected to a centrifugation process to remove the microorganism cells and the concentration of lactic acid contained in the supernatant was determined by using high performance liquid chromatography (Column: TSK gel ODS-80TM, Carrier: acetonitrile/water/trifluoroacetic acid=5/95/0.1). The accumulation of lactate ammonium salt at a level of 23% by weight was thereby determined. The yield was found to be 93%.

Corn steep liquer: 1.0% (Separately sterilized)
Sucrose: 1.0% (Separately sterilized)
Monopotassium phosphate: 0.1%
Dipotassium phosphate: 0.1%
NaCl: 0.02%
Magnesium sulfate 7 hydrates: 0.02%
Ferrous sulfate: 0.001% (Separately sterilized)
ε-caprolactam: 0.5%
pH: 7.2 (Adjusted with 2N sodium hydroxide)

EXAMPLE 3

According to the same procedure described in the example 2, NSSC 104 strain of Arthrobacter spp. was suspended in 0.1M phosphate buffer solution (pH 7.5) to prepare 4% by weight solution thereof on dry weight basis. Then, 2-hydroxy-4-methylthiobutyronitrile was added to the buffer solution to prepare 200 mM solution thereof as its final concentration, and the buffer solution was subjected to hydrolysis reaction at 30° C. with mild shaking. After the addition, the same amount of 2-hydroxy-4-methylthiobutyronitrile was repeatedly added to the hydrolyzed solution 7 times at an interval of 1 hour and further added 8 times at an interval of 1.5 hours to subject the solution to the reaction for total duration of 19 hours. After the completion of the reaction, the reacted-solution was centrifuged to remove microorganism cells, and the concentration of 2-hydroxy-4-methylthiobutyric acid contained in the supernatant was determined according to the same procedure as described in the example 1. The accumulation of 2-hydroxy-4-methylthiobutyrate ammonium salt at a level of 49% by weight was determined. The yield was found to be 96%.

EXAMPLE 4

According to the same procedure described in the example 2, NSSC 104 strain of Arthrobacter spp. was suspended in distillated water to prepare 3.2% by weight solution thereof on dry weight basis. Then, 2-hydroxy-4-methylthiobutyro nitrile was continuously added to the suspension at a rate of 0.46 g/hr per 1 g microorganism cells on dry weight basis. The suspension was then subjected to hydrolysis reaction at 30° C. for 20 hours while adjusting the pH with 0.5M aqueous ammonium solution to a range of from 7.4–7.6. After the completion of the reaction, the reacted-suspension was centrifuged to remove the microorganism cells. The microorganism cells collected was then washed 3 times with using 40-folds weight amount of distilled water, and the washed-cells were suspended again in distilled water in the same amount used for the first washing and was used for the second reaction. According to the same procedure for the first washing, all of the second reaction, recovery of microorganism cells and washing of microorganism cells were proceeded. After repeating such reaction process as described above 10 times, the concentration of 2-hydroxy-4-methylthiobutyric acid contained in the supernatant was determined for each replications according to the method as described in the example 1. The results are shown in the following table.

| Replication of Reaction | 2-hydroxy-4-methylthiobutyrate ammonium salt (% by weight) | Yield (%) |
| --- | --- | --- |
| 1 | 36.1 | 96 |
| 3 | 36.3 | 97 |
| 5 | 36.4 | 97 |
| 7 | 36.4 | 97 |
| 10 | 36.0 | 96 |

EXAMPLE 5

According to the same procedure described in the example 2, NSSC 104 strain of Arthrobacter spp. was suspended in 0.1M aqueous solution of sodium cyanide to prepare 5% by weight solution thereof on dry weight basis. Then, lactonitrile was continuously added to the solution and was then subjected to hydrolysis reaction at 30° C. for 10 hours while adjusting the pH by using a pH controller to a range of from 7.4–7.6. After the completion of the reaction, the reacted-solution was centrifuged to remove microorganism cells, and the concentration of lactic acid contained in the supernatant was determined according to the same procedure described in the example 2. Another reaction where the addition of sodium cyanide was omitted was also checked for the comparison. The results are shown in the following table.

| Amount of lactate ammonium salt produced (% by weight) | |
| --- | --- |
| No addition | 20.5 |
| 0.1 M NaCN | 40.0 |

EXAMPLE 6

According to the same procedure described in the example 2, NSSC 104 strain of Arthrobacter spp. was suspended in 0.1M aqueous solution of potassium cyanide to prepare 5% by weight solution thereof on dry weight basis. Then, 2-hydroxy-4-methylthiobutyronitrile was continuously added to the solution and was then subjected to hydrolysis reaction at 30° C. for 10 hours while adjusting the pH by using a pH controller to a range of from 7.4–7.6. After the completion of the reaction, the reacted-solution was centrifuged to remove microorganism cells, and the concentration of 2-hydroxy-4-methylthiobutyric acid contained in the supernatant was determined according to the same procedure described in the example 1. Another reaction where the addition of potassium cyanide was omitted was also checked for the comparison. The results are shown in the following table.

| Amount of 2-hydroxy-4-methylthiobutyrate ammonium salt (% by weight) | |
| --- | --- |
| No addition | 26.6 |
| 0.1M KCN | 41.7 |

EXAMPLE 7

According to the same procedure described in the example 2, NSSC 104 strain of Arthrobacter spp. was suspended in 40 mM aqueous solution of hydrogen cyanide to prepare 5% by weight solution thereof on dry weight basis. Then, 2-hydroxy-4-methylthiobutyronitrile was continuously added to the solution and was then subjected to hydrolysis reaction at 30° C. for 10 hours while adjusting the pH by using a pH controller to a range of from 7.4–7.6. After the completion of the reaction, the reacted-solution was centrifuged to remove microorganism cells, and the concentration of 2-hydroxy-4-methylthiobutyric acid contained in the supernatant was determined according to the same procedure described in the example 1. Another reaction where the addition of hydrogen cyanide was omitted was also checked for the comparison. The results are shown in the following table.

| Amount of 2-hydroxy-4-methylthiobutyrate ammonium salt produced (% by weight) | |
| --- | --- |
| No addition | 27.2 |
| 40 mM HCN | 44.5 |

Example for Comparison

The cultivation and the catalytic reaction of Arthrobacter NSSC 104 strain was carried out according to the cultivation method and the hydrolysis method described in Japanese Patent Laid-open No. Hei 4-40898.

(1) Medium (Unit: W/V)
Glycerol 2%
Yeast extract 0.3%
Monopotassium phosphate 0.68%
Dipotassium phosphate 0.71%
Sodium sulfate 0.28%
Magnesium chloride 0.04%
Calcium chloride 0.004%
Manganese sulfate 0.0004%
Ferrous chloride 0.00006%
Zinc sulfate 0.00005%
Agar 1.8%
α-chloropropionitrile 0.05%
pH 7.5

(2) Cultivating Condition

One loop amount of the microorganism cells was taken out of the medium and was inoculated onto agar plate medium, and then cultivated at 30° C. for 48 hours under aerobic condition.

(3) Hydrolysis Reaction

The microorganism cells was collected from the agar plate medium and then washed 3 times with 0.05M phosphate buffer (pH 7.5) by means of centrifugation.

The cells precipitated was re-suspended in 0.05M phosphate buffer in an amount of 1.5 ml so as to adjust the value of the OD 630 to 25, added with 100 mM 2-hydroxy-4-methylthiobutyronitrile as its final concentration and then allowed to a reaction at 25° C. for 20 hours under shaking condition. After the completion of the reaction, the reacted-solution was centrifuged to remove the microorganism cells, and the concentration of 2-hydroxy-4-methylthiobutyric acid contained in the supernatant was determined by using high performance liquid chromatography (Column: TSK gel ODS-80TM, Carrier: acetonitrile/water/trifluoroacetic acid=20/80/0.1). The concentration of 2-hydroxy-4-methylthiobutyric acid was 0.01 mM.

It is described in Japanese Patent Laid-open No. Hei 4-40898 that Arthrobacter HR4 strain achieved the accumulation of 2-hydroxy-4-methylthiobutyric acid at a level of 5 mM according to the cultivation method and the hydrolysis method as described above. Therefore, it is clearly indicated that Arthrobacter NSSC 104 strain is obviously different species from Arthrobacter HR4 strain.

Advantageous Effect of the Invention

According to the present invention, the production of α-hydroxy acid [II] in an efficient manner can be achieved by means of utilizing enzymatic reaction of microorganisms which can be repeatedly used, having both concentration resistance and durability against α-hydroxy nitrile [I] and/or α-hydroxy acid [II] and allows the accumulation of α-hydroxy acid [II] at a high concentration level. In addition, by adding a cyanide compound to the reaction system, the production of α-hydroxy acid [II] in more efficient manner can be achieved.

INDUSTRIAL USE OF THE INVENTION

The present invention is related to a process for producing α-hydroxy acid [II] by using α-hydroxy nitrile as the starting material in an industrial scale and by utilizing the enzymatic reaction of microorganisms which have both concentration resistance and durable property to α-hydroxy nitrile [I] and/or α-hydroxy acid [II], which provides great significance in the related-industry.

What is claimed is:

1. A method for producing compounds represented by a general formula [II], RCH(OH)COOH, wherein R represents a hydrogen atom, an optionally-substituted C1–C6 alkyl group, an optionally-substituted C2–C6 alkenyl group, an optionally-substituted C1–C6 alkoxy group, an optionally-substituted aryl group, an optionally-substituted aryloxy group or an optionally-substituted heterocyclic group, characterized in that a compound represented by a general formula [II], RCH(OH)COOH, wherein R is as defined above, is produced and accumulated in an aqueous solvent in the presence of Variovorax spp. or Arthrobacter NSSC 104 strain in the process for converting a compound represented by a general formula [I], RCH(OH)CN, wherein R is as defined above, to a compound represented by a general formula [II], RCH(OH)COOH, wherein R is as defined above, by utilizing hydrolytic reaction provided by the enzymatic activity of the specific microorganisms.

2. A method for producing compounds represented by a general formula [II], RCH(OH)COOH according to claim 1, wherein R is a hydrogen atom, an optionally-substituted C1–C6 alkyl group or an optionally-substituted phenyl.

3. A method for producing compounds represented by a general formula [II], RCH(OH)COOH, according to claim 1 or 2, wherein R is a hydrogen atom, a C1–C6 alkylthio alkyl group, a C1–C6 hydroxy alkyl group or phenyl.

4. A method for producing compounds represented by the general formula [II], RCH(OH)COOH, according to claim 1, wherein the compound represented by a general formula [I], RCH(OH)CN, is selected from a group consisting of lactonitrile, mandelonitrile and 2-hydroxy-4-methylthiobutyronitrile.

5. Arthrobacter NSSC 104 strain, having concentration resistance and durable property to compounds represented by a general formula [I], RCH(OH)CN wherein R represents a hydrogen atom, an optionally-substituted C1–C6 alkyl group, an optionally-substituted C2–C6 alkenyl group, an optionally-substituted C1–C6 alkoxy group, an optionally-substituted aryl group, an optionally-substituted aryloxy group or an optionally-substituted heterocyclic group, and/or compounds represented by a general formula [II], RCH(OH)COOH and having capability to convert a compound represented by a general formula [I], RCH(OH)CN, wherein R is as defined above, to a compound represented by a general formula [II], RCH(OH)COOH.

6. A method for producing compounds represented by a general formula [II], RCH(OH)COOH, wherein R represents a hydrogen atom, an optionally-substituted C1–C6 alkyl group, an optionally-substituted C2–C6 alkenyl group, an optionally-substituted C1–C6 alkoxy group, an optionally-substituted aryl group, an optionally-substituted aryloxy group or an optionally-substituted heterocyclic group, characterized in that, in the method for producing compounds represented by a general formula [II], RCH(OH)COOH wherein R is as defined above, based on hydrolysis of a compound represented by a general formula [I], RCH(OH)CN wherein R is as defined above, by means of utilizing the enzymatic activity of Variovorax spp. or Arthrobacter NSSC 104 strain, the reaction is proceeded in the presence of a cyanide compound represented by a general formula [III], Mm(CN)n wherein M represents a hydrogen atom, ammonium or a metal ion, and m and n each independently represent an integer 1, 2 or 3.

7. A method for producing compounds by a general formula [II], RCH(OH)COOH, according to claim 6, wherein R is hydrogen, an optionally-substituted C1–C6 alkyl group or an optionally-substituted phenyl.

8. A method for producing compounds represented by a general formula [II], RCH(OH)COOH, according to claim 6 or 7, wherein R is hydrogen, an C1–C6 alkylthioalkyl group, C1–C6 hydroxy alkyl group or phenyl.

9. A method for producing compounds represented by a general formula [II], RCH(OH)COOH, according to claim 6, wherein a compound represented by a general formula [I], RCH(OH)CN, wherein R is as defined above, is one selected from a group consisting of lactonitrile, mandelonitrile and 2-hydroxy-4-methylthiobutyronitrile.

* * * * *

UNITED STATES PATENT AND TRADEMARK OFFICE
CERTIFICATE OF CORRECTION

PATENT NO : 6,037,155
DATED : March 14, 2000
INVENTOR(S) : Yoichi Kobayashi, et al.

It is certified that error appears in the above-identified patent and that said Letters Patent is hereby corrected as shown below:

On title page, item 75 Inventors
replace "Fujiwasa"
with --Kanagawa--.

On title page, item 75 Inventors
replace "Yokohama"
with --Kanagawa--.

On title page, item 75 Inventors
replace "Hiratsuka"
with --Kanagawa--.

Signed and Sealed this

Sixth Day of February, 2001

*Attest:*

Q. TODD DICKINSON

*Attesting Officer*    *Director of Patents and Trademarks*